US 6,650,408 B2

(12) United States Patent
Jun et al.

(10) Patent No.: US 6,650,408 B2
(45) Date of Patent: Nov. 18, 2003

(54) METHOD FOR INSPECTING A POLISHING PAD IN A SEMICONDUCTOR MANUFACTURING PROCESS, AN APPARATUS FOR PERFORMING THE METHOD, AND A POLISHING DEVICE ADOPTING THE APPARATUS

(75) Inventors: Chung-Sam Jun, Whasung-gun (KR); Kye-Weon Kim, Suwon-si (KR); Yu-Sin Yang, Yongin-si (KR); Hyo-Hoo Kim, Anyang-si (KR)

(73) Assignee: Samsung Electronics Co., Ltd., Suwon (KR)

( * ) Notice: Subject to any disclaimer, the term of this patent is extended or adjusted under 35 U.S.C. 154(b) by 82 days.

(21) Appl. No.: 09/988,683

(22) Filed: Nov. 20, 2001

(65) Prior Publication Data
US 2002/0063860 A1 May 30, 2002

(30) Foreign Application Priority Data
Nov. 24, 2000 (KR) ........................ 2000-70546

(51) Int. Cl.[7] ............................... G01N 21/00
(52) U.S. Cl. ................... 356/237.2; 356/237.1
(58) Field of Search ............... 356/237.1, 237.2, 356/237.3, 237.4, 237.5, 237.6, 394, 503; 250/559.14, 559.22, 559.27; 451/6–8

(56) References Cited

U.S. PATENT DOCUMENTS

| 5,708,506 | A | | 1/1998 | Birang |
| 5,961,369 | A | * | 10/1999 | Bartels et al. ............... 451/8 |
| 6,028,669 | A | * | 2/2000 | Tzeng ....................... 356/503 |
| 6,045,434 | A | | 4/2000 | Fisher, Jr. et al. |
| 6,108,093 | A | * | 8/2000 | Berman ..................... 356/394 |
| 6,143,123 | A | * | 11/2000 | Robinson et al. ........... 156/344 |
| 6,165,050 | A | * | 12/2000 | Ban et al. ..................... 451/8 |
| 6,201,253 | B1 | * | 3/2001 | Allman et al. ......... 250/559.27 |

FOREIGN PATENT DOCUMENTS

| JP | 1997-285955 A | 11/1997 |
| KR | 1999-025212 | 4/1999 |

* cited by examiner

Primary Examiner—Frank G. Font
Assistant Examiner—Sang H. Nguyen
(74) Attorney, Agent, or Firm—Volentine Francos, PLLC

(57) ABSTRACT

A method for inspecting a polishing pad, an apparatus for performing the method, and a polishing device adopting the apparatus for preventing wafer defects. Polishing pad defects are detected by comparing optical data from a normal polishing pad, which does not cause wafer defects, with optical data from a polishing pad to be inspected. The respective optical data are obtained by radiating a beam into the polishing pad and then collecting and analyzing a beam reflected from the polishing pad.

19 Claims, 14 Drawing Sheets

METHOD FOR INSPECTING A POLISHING PAD IN A SEMICONDUCTOR MANUFACTURING PROCESS, AN APPARATUS FOR PERFORMING THE METHOD, AND A POLISHING DEVICE ADOPTING THE APPARATUS

BACKGROUND OF THE INVENTION

1. Field of the Invention

The present invention relates to a method for inspecting a polishing pad, an apparatus for performing the method of inspecting, and a polishing device adopting the apparatus, which can prevent wafer defects during wafer polishing operations.

2. Description of the Related Art

During a conventional semiconductor manufacturing procedure, processes such as lithography, light exposure, ion implantation, chemical and mechanical polishing, chemical or physical deposition, and plasma etching, are performed on wafers to form semiconductor chips and devices. In particular, chemical and mechanical polishing processes are widely used for manufacturing the semiconductor device, because the chemical and mechanical polishing process can be carried out at a low temperature and a large area of the wafer can be planarized.

FIG. 1 shows a conventional polishing device for manufacturing a semiconductor device. In FIG. 1, a platen 12 is provided with a polishing pad 10 which makes contact with a wafer W. A motor 14 rotates the platen 12, so that the polishing pad 10 attached on the platen 12 polishes the wafer W. A polishing head 16 fixes the wafer W via suction during the polishing process. The polishing head 16 rotates while urging the wafer W toward the platen 12. A polishing pad conditioner 18 is installed along a side of the polishing pad 10 for periodically conditioning the polishing pad 10. The polishing pad conditioner 18 is pressed toward the polishing pad 10, and is conditioned by means of a diamond disc formed within the surface of the polishing pad conditioner 18. A slurry supply 20 provides slurry to the polishing pad 10 during the polishing operation.

In operation, polishing head 16 fixes the wafer W in place via suction, then the polishing head 16 and the polishing pad 10 are rotated so as to allow the wafer W to contact the polishing pad 10. At the same time, the slurries are supplied onto the polishing pad 10 and the slurries are distributed radially outward along the polishing pad 10 surface as a result of the rotation of the polishing pad 10, thereby promoting the polishing of the wafer W. The polishing pad conditioner 18 is brought into contact with the polishing pad 10 at periodic intervals so as to prevent the polishing pad from wearing unevenly.

While the polishing process can planarize a large area of the wafer W, there is a drawback. Since the polishing pad 10 directly contacts the wafer W, the wafer W may be scratched if the surface of the polishing pad 10 has a defect, or particles introduced from the exterior are attached on the surface of the polishing pad 10. Such defects can lower the production yield of the semiconductor device.

Typically, in order to check for defects on the polishing pad 10, an operator examines the polishing pad 10 with the naked eye, or the operator inspects the surface of the wafer W after the polishing process has been finished. However, checking the polishing pad 10 with the naked eye takes a lot of time, and it is difficult to attain an accurate measurement because of the vagaries inherent in a process requiring human intervention.

Various kinds of solutions have been disclosed in an effort to prevent the wafer from being scratched during the polishing process. For example, in U.S. Pat. No. 5,708,506 issued to Birang, the roughness of the surface of the polishing pad is measured using an optical device so as to control the conditioning process to prevent wear on the polishing pad. U.S. Pat. No. 6,045,434 issued to Fisher, Jr. et.al., discloses an apparatus for conditioning the polishing pad by measuring the variation of the thickness of the polishing pad during the polishing process. Also, Korean Patent Laid-Open Publication No. 1999-25212 discloses a method for determining the replacement period of the polishing pad by measuring the profile of the polishing pad.

However, though the above apparatuses can improve the surface uniformity and control the thickness of the wafer, scratches may still be generated on the surface of the wafer.

SUMMARY OF THE INVENTION

In view of the shortcomings and drawbacks of the prior art, it is an object of the present invention to provide a method for inspecting a polishing pad so as to reduce wafer defects during a polishing process.

Another object of the present invention is to provide an apparatus for inspecting the polishing pad so as to reduce wafer defects during the polishing process.

Still another object of the present invention is to provide a polishing device which polishes the wafer while inspecting the polishing pad.

To accomplish the first object of the present invention, there is provided a method for inspecting a polishing pad. According to the method, reference data are obtained from a surface of a normal polishing pad, which does not generate wafer defects during the polishing process. Empirical data are then obtained from a surface of a polishing pad to be inspected. Then, the state of the polishing pad is determined by comparing the reference data of the normal polishing pad with the empirical data of the polishing pad to be inspected.

To accomplish the second object of the present invention, there is provided an apparatus for inspecting a polishing pad including an optical data gathering part for obtaining optical data from two sources: (1) reference data from a surface of a normal polishing pad, which does not generate wafer defects during the polishing process, and (2) empirical data from a surface of a polishing pad to be inspected. A defect profile, or defect state, is attained by comparing the reference data with the empirical data of the polishing pad outputted from the optical data gathering part.

To accomplish the third object of the present invention, there is provided a polishing device including a polishing head which fixes a wafer thereto via suction, and rotates the wafer while pressing the wafer against a polishing pad positioned in a platen. The platen is also rotated by a rotating shaft attached thereto. An optical data gathering part obtains optical data from two sources: (1) reference data from a surface of a normal polishing pad, which does not generate wafer defects during the polishing process, and (2) empirical data from a surface of a polishing pad to be inspected. A defect profile, or defect state, is attained by comparing the reference data with the empirical data of the polishing pad outputted from the optical data gathering part.

The polishing pad is preferably inspected for defects before the polishing pad is placed on the polishing device so as not to cause wafer defects while the inspection is being conducted. The operator can also choose to inspect the polishing pad for defects during any idle time of the polishing process, or after the polishing process. In this way, the operator can quickly take follow-up measures when a defect is found in the polishing pad. Accordingly, the wafer is prevented from being scratched during the polishing process.

BRIEF DESCRIPTION OF THE DRAWINGS

The above objects and other advantages of the present invention will become more apparent by describing in detail a preferred embodiment thereof with reference to the attached drawings, in which.

DETAILED DESCRIPTION OF PERFERRED EMBODIMENTS

Figure 1:
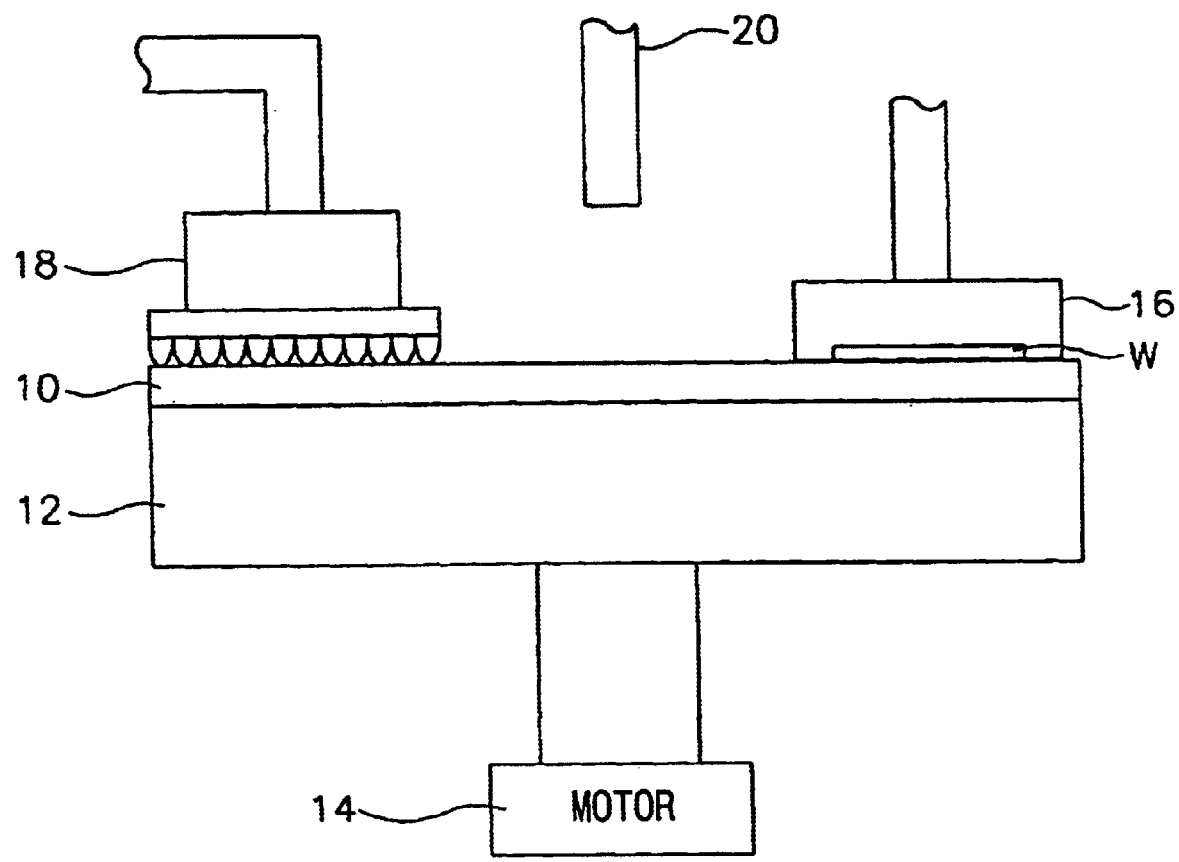
FIG. 1 is a schematic view showing the structure of a conventional polishing device.

The present invention now will be described more fully with reference to the accompanying drawings, in which preferred embodiments of the invention are shown. The invention may, however, be embodied in many different forms and should not be construed as being limited to the embodiments set forth herein; rather, these embodiments are provided so that this disclosure will be thorough and complete, and will fully convey the concept of the invention to those skilled in the art. In the drawings, the thickness of layers and regions are exaggerated for clarity.

Figure 2:
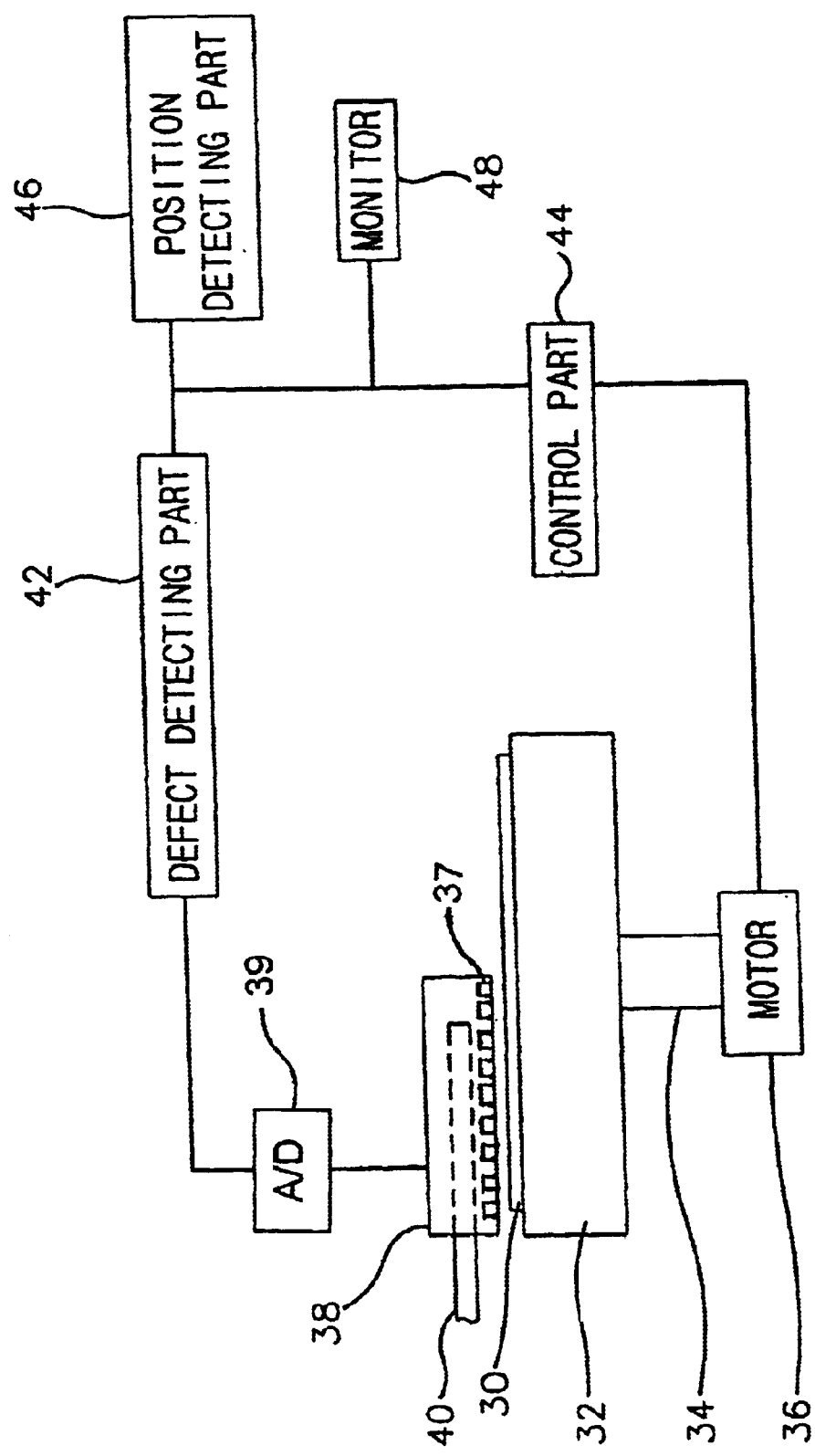
FIG. 2 is a schematic view showing the structure of an apparatus for inspecting a polishing pad according to an embodiment of the present invention.
Figure 3:
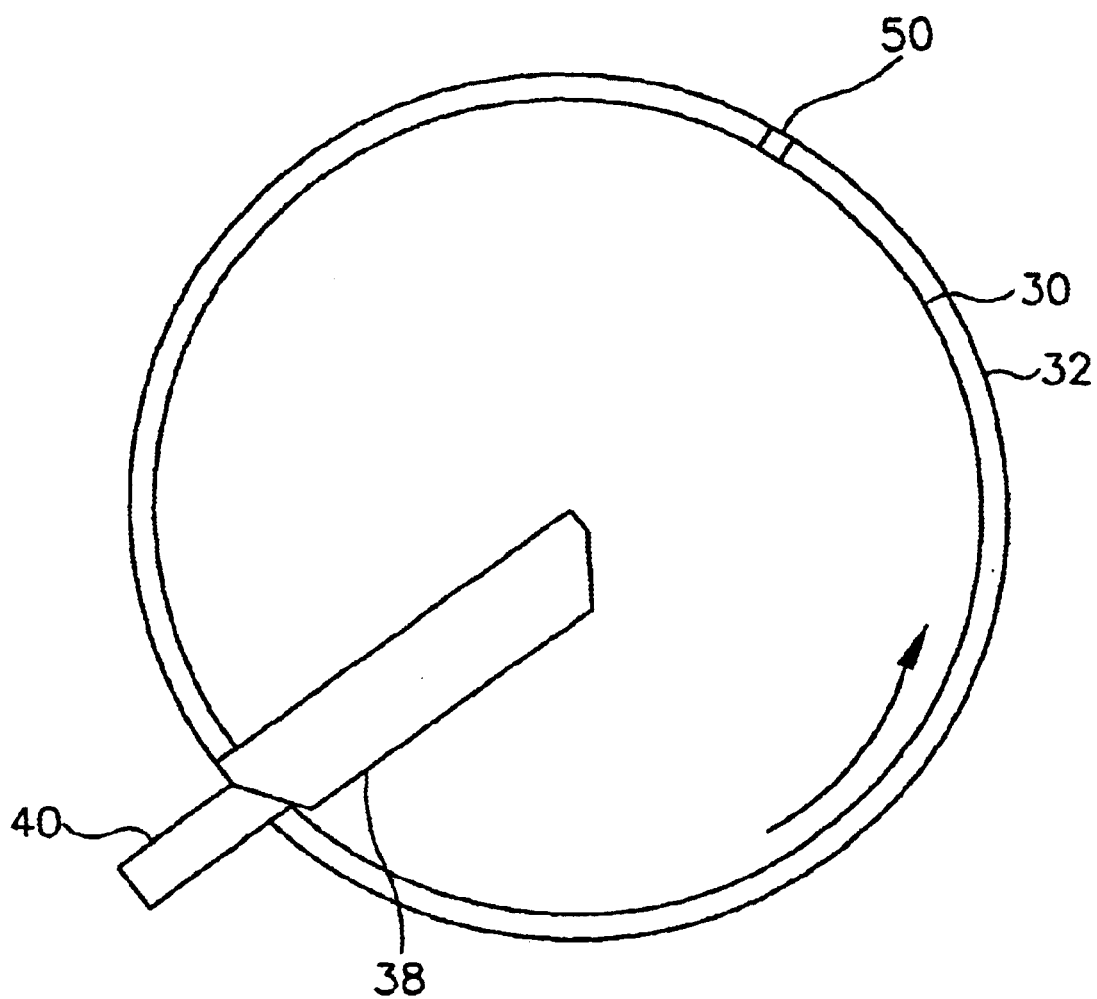
FIG. 3 is a plan view showing the apparatus for inspecting the polishing pad according to the embodiment of FIG. 2.

FIGS. 2 and 3 illustrate an apparatus for inspecting a polishing pad according to an embodiment of the present invention. FIG. 2 is a schematic view showing the structure of an apparatus for inspecting the polishing pad, and FIG. 3 is a plan view showing the apparatus for inspecting the polishing pad.

Referring to FIGS. 2 and 3, the polishing pad 30 is placed on a stage 32. A rotating shaft 34, positioned at a lower portion of the stage 32, is connected to a motor 36 to rotate stage 32. An optical data gathering part 38 positioned above the polishing pad 30 acquires optical data from a surface of the polishing pad 30 by using an optical beam. The optical data gathering part 38 is supported by a supporter 40 in such a manner that the optical data gathering part 38 can be spaced from an upper portion of the polishing pad 30.

Generally, the optical data gathering part 38 includes a beam source, for radiating the beam onto a predetermined portion or sector of the surface of the polishing pad 30, and a beam collecting part, for collecting a reflection beam reflected from the polishing pad 30.

An output part is connected to the beam collecting part so as to output an intensity of the collected beam. The output part has a plurality of opto-electric converting devices 37 for converting the reflected beam from the beam collection part to electric signals, where the intensity of the beam is outputted as analog signals. The output part also includes an A/D converter 39 for converting an analog signal to a digital signal or vice versa. The polishing pad has a circular shape and the plurality of opto-electric devices 37 can be arranged in such a manner that they are spaced from a center of the polishing pad and have predetermined angles. The structure of the optical data gathering part 38 is described in greater detail later.

When the stage 32 rotates, the polishing pad 30 placed on the stage 32 is also rotated. The optical data gathering part 38 continuously radiates the beam towards the polishing pad 30 being rotated and collects the reflection beam reflected from the polishing pad 30. In addition, the optical data gathering part 38 continuously outputs the optical data with respect to the intensity of the collected beam. While the optical data gathering part 38 optimally radiates the beam onto a portion or sector of the polishing pad 30 as described above, it is understood that the optical data regarding the whole surface of the polishing pad can be obtained simultaneously by continuously obtaining the optical data from the entire polishing pad while rotating the polishing pad 30.

Figure 4:
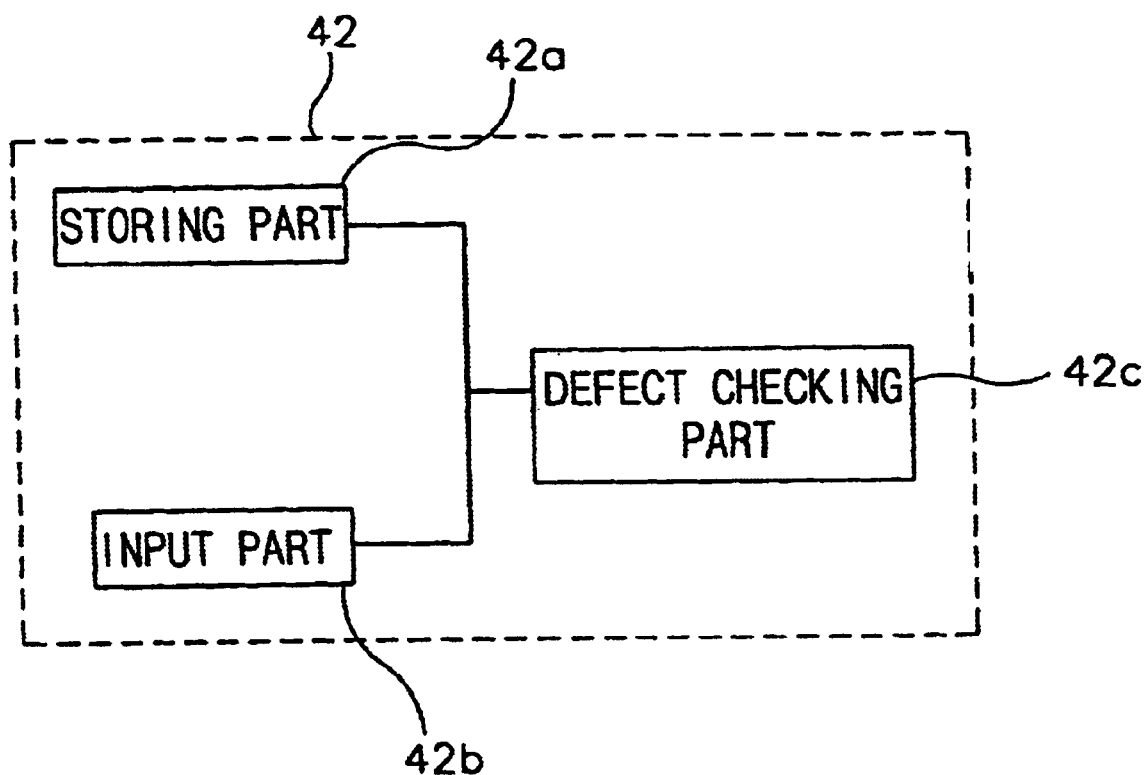
FIG. 4 is a block diagram showing a defect detecting part of the apparatus shown in FIG. 2.

A defect detecting part 42 is provided to detect polishing pad defects by using and comparing the optical data outputted from the optical data gathering part 38. FIG. 4 shows the structure of the defect detecting part 42 shown in FIG. 2.

Referring to FIG. 4, the defect detecting part 42 includes a storing part 42a for storing the optical data outputted from a surface of a normal polishing pad, which does not generate wafer defects during the polishing process. The optical data stored in the storing part 42a are reference data for determining whether or not defects exist on the polishing pad 30.

The defect detecting part 42 also includes an input part 42b into which the optical data is continuously inputted from the polishing pad to be inspected, as gathered by the optical data gathering part 38.

A defect checking part 42c checks for defects on the polishing pad being inspected. The defect detecting part 42 compares the reference optical data stored in the storing part 42a with the empirical optical data of the analog signal inputted into the input part 42b, as gathered from the optical data gathering part 38. If the difference between the reference optical data of the storing part 42a and the empirical optical data of the input part 42b exceeds a predetermined value, the defect checking part 42c determines that the polishing pad 30 has a defect.

In addition to the comparison function, the defect checking part 42c performs arithmetic functions for a smoothing process, in which the optical data of the reference data and the empirical data is divided into a plurality of data areas so as to obtain an average data value from the data areas.

As shown in FIG. 2, a control part 44 is connected to the defect detecting part 42. When the defect is detected by the defect detecting part 42, the control part 44 stops the operation of the apparatus, including the stage 32 and the optical data gathering part 38, and generates an alarm signal.

A position detecting part 46 is connected to the defect detecting part 42 so as to detect the location of the defect in the polishing pad 30 being inspected. The position detecting part 46 calculates both a rotating angle of the stage 32 with respect to a reference point 50 (see FIG. 3), which is positioned at an edge of the polishing pad 30 or at a predetermined portion of the stage 32, and a distance from a center of the polishing pad 30 so as to detect the location of the defect.

A monitor 48 is connected to the defect detecting part 42 so as to display the defect state of the polishing pad to be inspected. The monitor 48 displays the optical data outputted from the optical data gathering part 38 and the defects, if any, existing in the polishing pad 30. Accordingly, the operator can check the optical data for the existence of defects, and can then rapidly remove the defect when the defect is generated.

Figure 5:
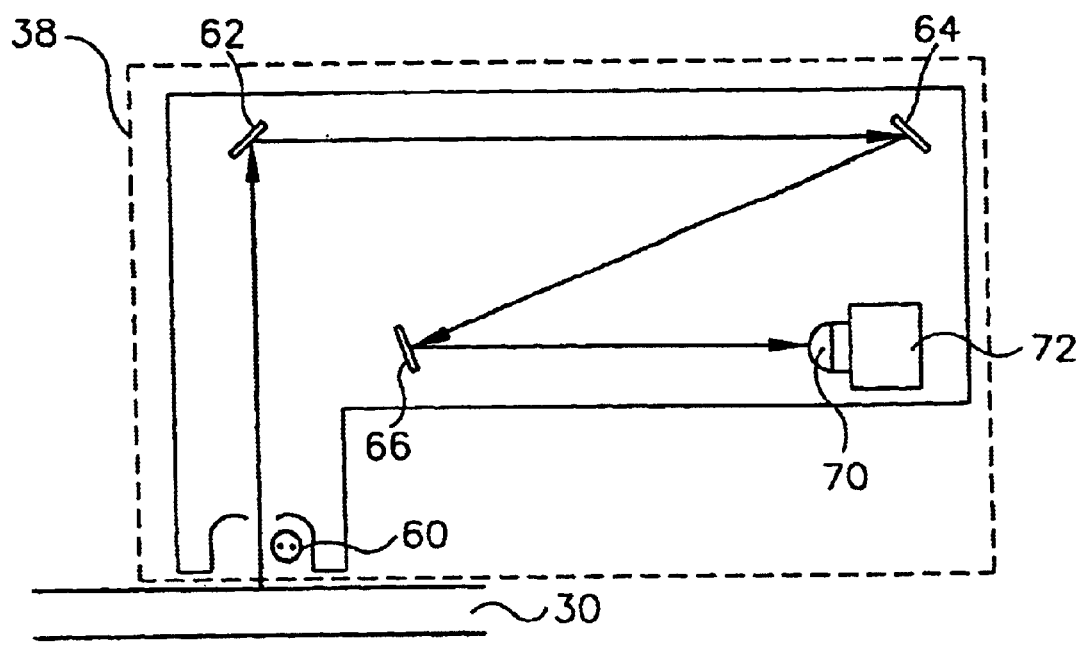
FIG. 5 is a schematic view showing an optical data gathering part of the apparatus shown in FIGS. 2 and 3.

FIG. 5 illustrates the optical data gathering part 38 in greater detail. As described above, the optical data gathering part 38 has a beam source 60 for radiating the beam onto the polishing pad 30 to check for defects. The radiated beam is reflected from the surface of the polishing pad 30 toward a first reflecting plate 62 and then onto a second reflecting plate 64. Then, the beam is reflected from the second reflecting plate 64 toward a third reflecting plate 66. The beam reflected from the third reflection plate 66 is collected in the beam collecting part 70. The beam collecting part 70 includes a lens. The output part 72, which is provided with the plurality of opto-electric converting devices as described previously, is positioned at a rear portion of the collecting part 70. The output part 72 outputs the optical data as an analog signal representing the intensity of the beam.

Figure 6A:
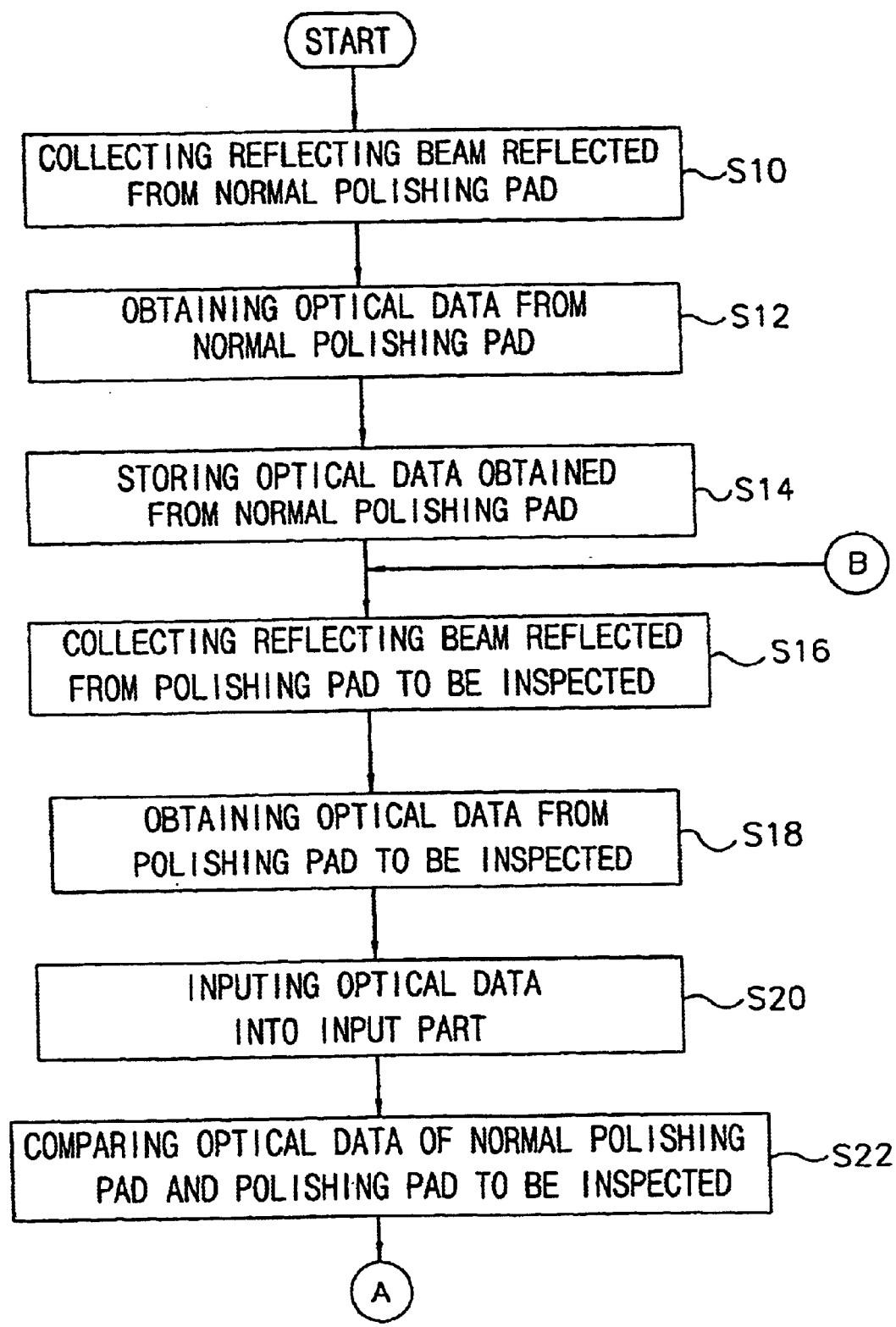
FIGS. 6A and 6B are flow charts showing a method for inspecting the polishing pad according to an embodiment of the present invention.
Figure 6B:
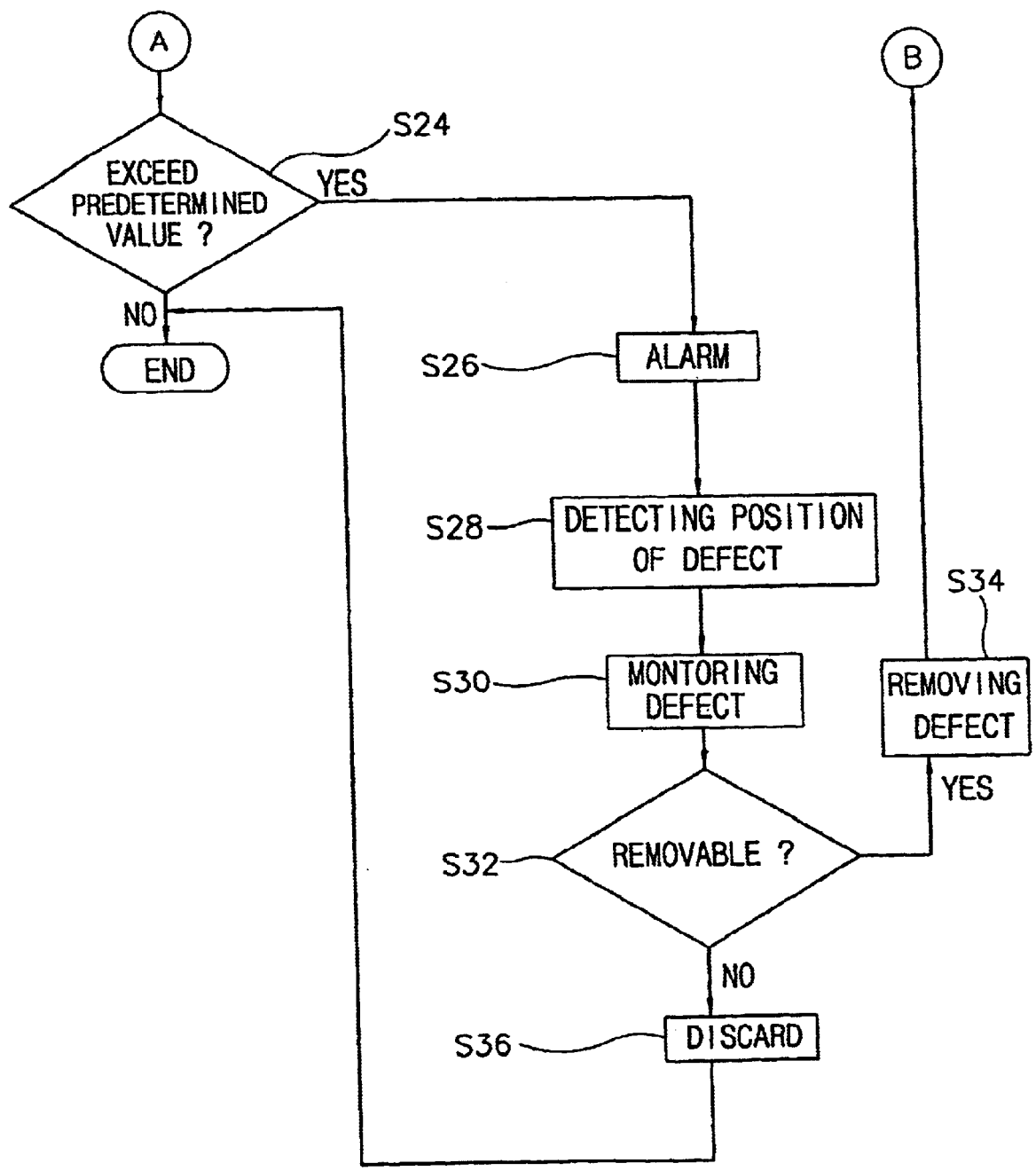

FIGS. 6A and 6B are flow charts showing a method for inspecting the polishing pad according to an embodiment of the present invention. The method for inspecting the polishing pad will be described in conjunction with the apparatus for inspecting the polishing pad shown in FIGS. 2 to 5, although it is understood that the method may be performed with other suitable polishing equipment and apparatus.

Referring to FIGS. 6A and 6B, the beam source 60 of the optical data gathering part 38 radiates a beam onto a normal polishing pad. A normal polishing pad as described within the context of the present invention is a polishing pad that does not produce defects in a wafer during the polishing process. The beam is reflected from the normal polishing pad, and collected in the beam collecting part 70 (step S10). Then (step S12), the output part 72 outputs the optical data, which optical data represents the intensity of the collected beam, to the defect detecting part 42. To generate the optical data, the intensity of the collected beam is converted into the electric signal by the opto-electric converting devices in the output part 72, so analog signals are outputted as the output data. Of course, using a converter, it is possible to convert the analog optical data signals into digital optical data signals. The analog or digital optical data signals obtained from the normal polishing pad (i.e., reference data) are stored in the storing part 42a of the defect detecting part 42 (step S14).

Thereafter, the beam source 60 of the optical data gathering part 38 radiates the beam onto the portion or sector of the polishing pad to be inspected, and the reflected beam is collected in the beam collecting part 70 (step S16). The output part 72 outputs the optical data representing the intensity of the collected beam (step S18) to the defect detecting part 42. The intensity of the collected beam is converted into the electric signal by the opto-electric converting devices within the output part 72, so analog signals are outputted as the output data. Of course, using a converter, it is possible to convert the analog optical data signals into digital optical data signals. The analog or digital optical data signals obtained from the polishing pad to be inspected (i.e., empirical data) are inputted into the input part 42b of the defect detecting part 42 (step S20).

Then, the reference optical data from the normal polishing pad stored in the storing part 42a and the empirical optical data from the polishing pad to be inspected resident in the input part 42b are compared by means of the defect checking part 42c (step S22). If the difference between the optical data of the storing part 42a and the input part 42b exceeds a predetermined value, the defect checking part 42c determines that the polishing pad 30 has a defect (step S24).

Since grooves are formed on the polishing pad 30 to allow the slurries to flow along the polishing pad 30, the optical data representing the intensity of the reflected beam are regularly varied by the grooves. Therefore, irregular optical data causing polishing pad defects can be discriminated from the regular optical data obtained from the normal polishing pad. However, the variation of the optical data caused by the grooves may reduce the ability to detect the defect. Therefore, in order to improve the ability to detect the defect, a smoothing treatment for increasing the signal to noise ratio is carried out. Specifically, the optical data of the analog signal are divided into a plurality of data areas so as to obtain an average data value from the data areas. The average data value is then compared with the optical data of the polishing pad to determine whether a defect is present.

If the smoothing treatment is carried out with respect to the optical data obtained from the polishing pad to be inspected and the normal polishing pad, the difference in the optical data value between a defect-free area of the polishing pad to be inspected and the normal polishing pad is reduced. Furthermore, the difference in the optical data value between a defect-present area of the polishing pad to be inspected and the normal polishing pad is increased so that the defect can be easily detected.

Preferably, the defect inspection is carried out with respect to the whole polishing pad 30 to be inspected. For this reason, the optical data are continuously obtained from predetermined areas of the polishing pad 30 while varying the inspection areas of the polishing pad 30, thereby obtaining the optical data from the whole polishing pad 30 to be inspected. The optical data obtained from the whole polishing pad 30 to be inspected are compared with the optical data obtained from the normal polishing so that the defects can be detected.

In order to obtain the optical data from the whole polishing pad 30 to be inspected, the polishing pad 30 placed on the stage 32 is rotated and the optical data gathering part 38 radiates the beam along the radius area of the polishing pad 30, thereby collecting and outputting the optical data representing the intensity of the reflection beam. By continuously obtaining the optical data from the rotating polishing pad 30 to be inspected, the optical data with respect to the whole polishing pad 30 can be obtained. Note that the optical data can be converted into digital signals by the plurality of opto-electric converting devices.

If the defect detecting part 42 determines that the polishing pad 30 is defect-free, the polishing pad inspection is completed. However, if the defect detecting part 42 determines that the polishing pad 30 has a defect, the control part 44 stops the operation of the stage 32 and the optical data gathering part 38 and generates an alarm signal (step S26).

Then, the position of the existing defect on the polishing pad 30 to be inspected is determined by the position detecting part 46 (step S28). The position of the defect can be obtained by calculating the rotating angle of the polishing pad 30, with respect to the reference point 50, and the distance from the center of the polishing pad 30.

The detected defect is displayed on the monitor 48 which is connected to the defect detecting part 42 so as to allow the operator to view the defect state of the polishing pad and recognize the defect (step S30). If the defect is displayed on the monitor 48, the operator physically inspects the polishing pad 30 to be inspected.

During the physical inspection, the operator determines whether or not the defect can be removed (step S32). If the defect is generated by impurities attached on the polishing pad 30, the defect may be removable, and the operator will do so (step 34). However, if the defect is generated by a tearing of the polishing pad 30, or impurities which are introduced into the polishing pad 30 when the polishing pad 30 is manufactured, it would be difficult to remove the defect. If the defect is not removable, the polishing pad 30 is discarded (step S36).

If the same polishing pad is again inspected, the optical data from the normal polishing pad can be reused, so the defect is determined only by obtaining the optical data from the polishing pad to be inspected.

Figure 7:
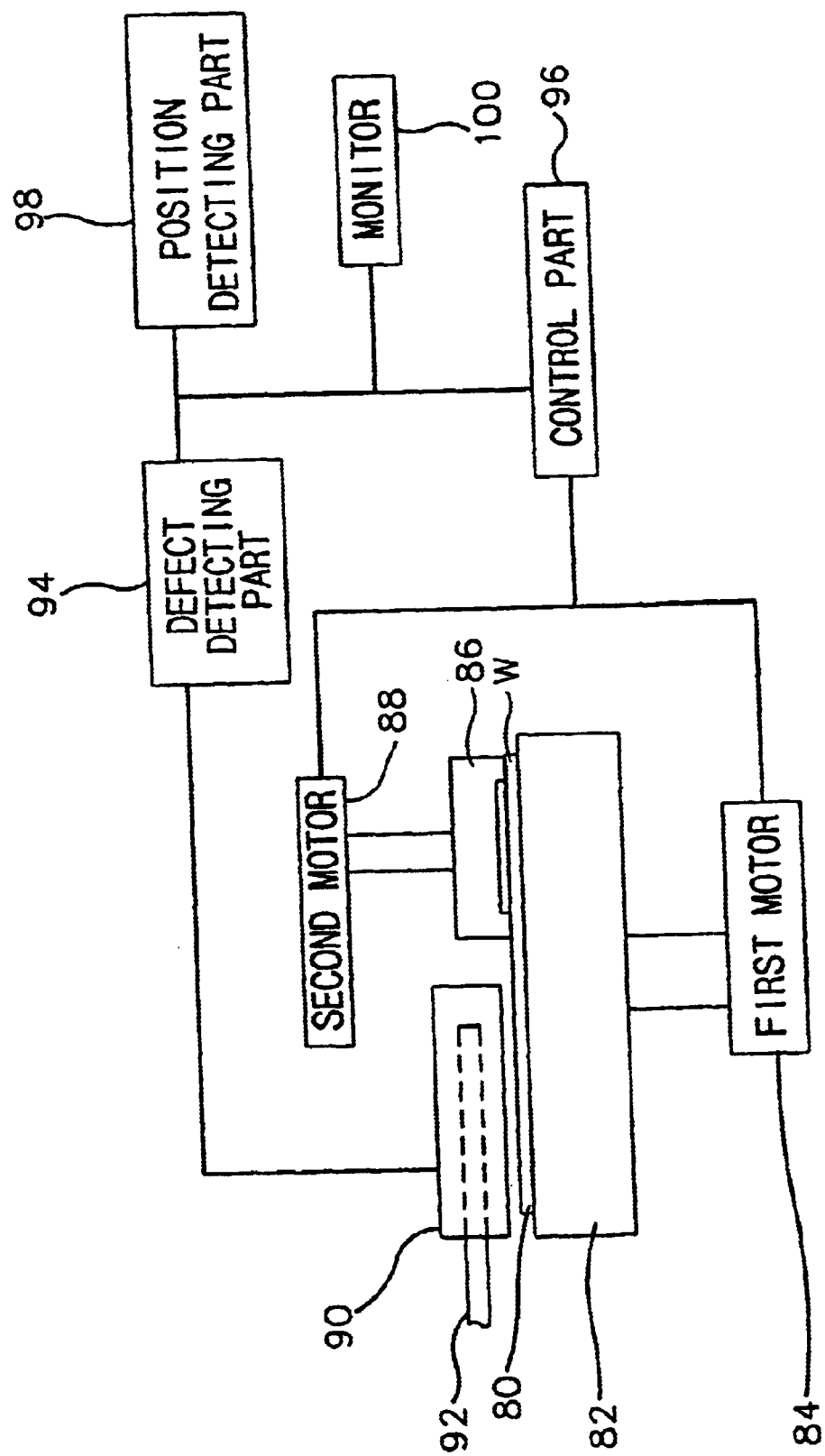
FIG. 7 is a schematic view showing a polishing device according to an embodiment of the present invention.
Figure 8:
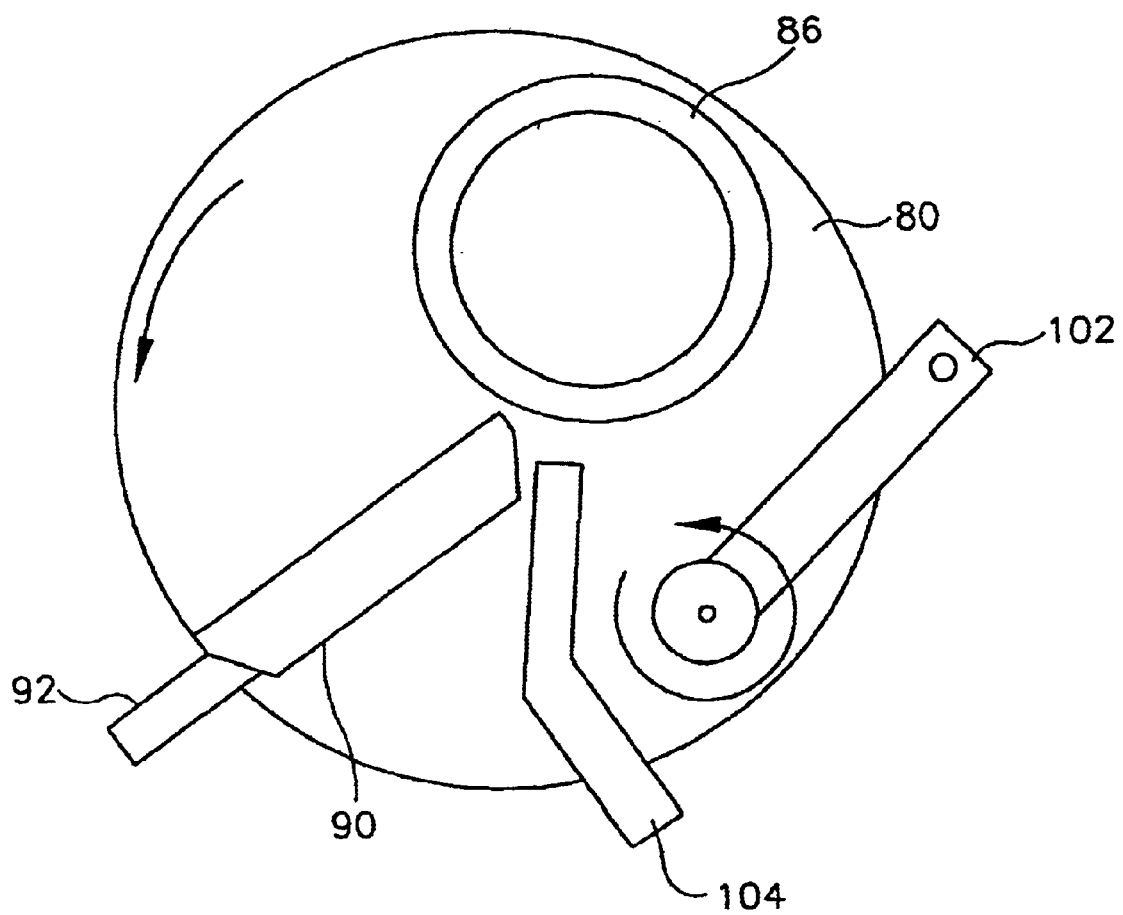
FIG. 8 is a plan view showing the polishing device according to an embodiment of the present invention.

FIGS. 7 and 8 show a polishing device adopting the apparatus for inspecting the polishing pad according to an embodiment of the present invention. Referring to FIGS. 7 and 8, a polishing pad 80 placed on a platen 82 makes contact with a wafer W. A first motor 84 rotates the platen 82 and the polishing pad 80 attached thereon. The polishing pad 80 is formed with grooves so as to allow slurries to flow along the polishing pad 80. A polishing head 86 fixes the wafer W in place via suction, and then rotates the wafer W using a second motor 86 while pressing the wafer W against the polishing pad 80. A polishing pad conditioner 102 is installed adjacent to the polishing pad 80 for conditioning the polishing pad 80. The conditioning of the polishing pad 80 is carried out using a diamond disc disposed at a lower portion of the polishing pad conditioner 102. In operation, the diamond particles attached to the diamond disc are pressed against the polishing pad 80, thereby conditioning the polishing pad 80 by removing a selected portion of the polishing pad layer. In addition, a slurry supplying part 104 for supplying slurries onto the polishing pad is installed above the polishing pad 80.

An optical data gathering part 90 is provided for obtaining optical data from the polishing pad 80 by radiating a beam into a surface of the polishing pad 80. A supporter 92 supports the optical data gathering part 90 such that the optical data gathering part 90 is spaced from the upper portion of the polishing pad 80. A defect detecting part 94 is provided to detect polishing pad defects by comparing the optical data outputted from the optical data gathering part 90.

The basic structures and functions of the optical data gathering part 90, defect detecting part 94, control part 96, position detecting part 98, and monitor 100, are identical to the structures and functions of the optical obtaining part 38, defect detecting part 42, control part 44, position detecting part 46, and monitor 48, respectively, shown in the FIGS. 2 and 3, and are therefore not repeated here for simplicity.

Note that when a defect is detected by the defect detecting part 94, the control part 96 sends control signals to the first and second motors 84 and 88 so as to stop the operation of the platen 82 and the polishing head 86 and generates an alarm signal.

As stated above, an operator can check for defects before the polishing process starts, during the idling time of the polishing process, and after the polishing process is complete. The idling time includes the time required for the polishing head 86 to move the wafer to another polishing pad 80 when the polishing process is carried out by using a plurality of polishing pads 80. Therefore, the operator can rapidly inspect the polishing pad 80 for foreign particles, such as diamond particles from the diamond disc and impurities caused by the solidified slurries, that may be formed on the surface of the polishing pad 80. Accordingly, wafer defects caused by polishing pad defects can be greatly reduced.

Figure 9A:
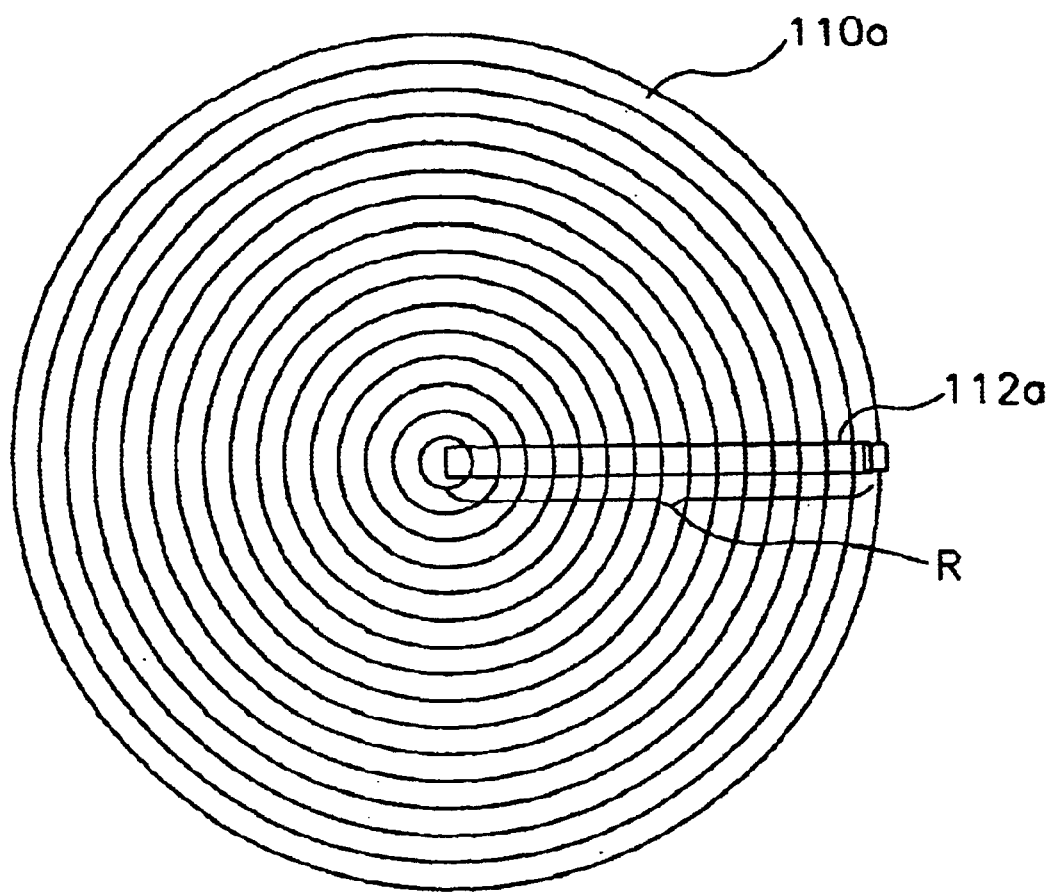
FIGS. 9A and 9B are views showing images of outputted data which are obtained by inspecting the polishing pad according to the method of the present invention.
Figure 9B:
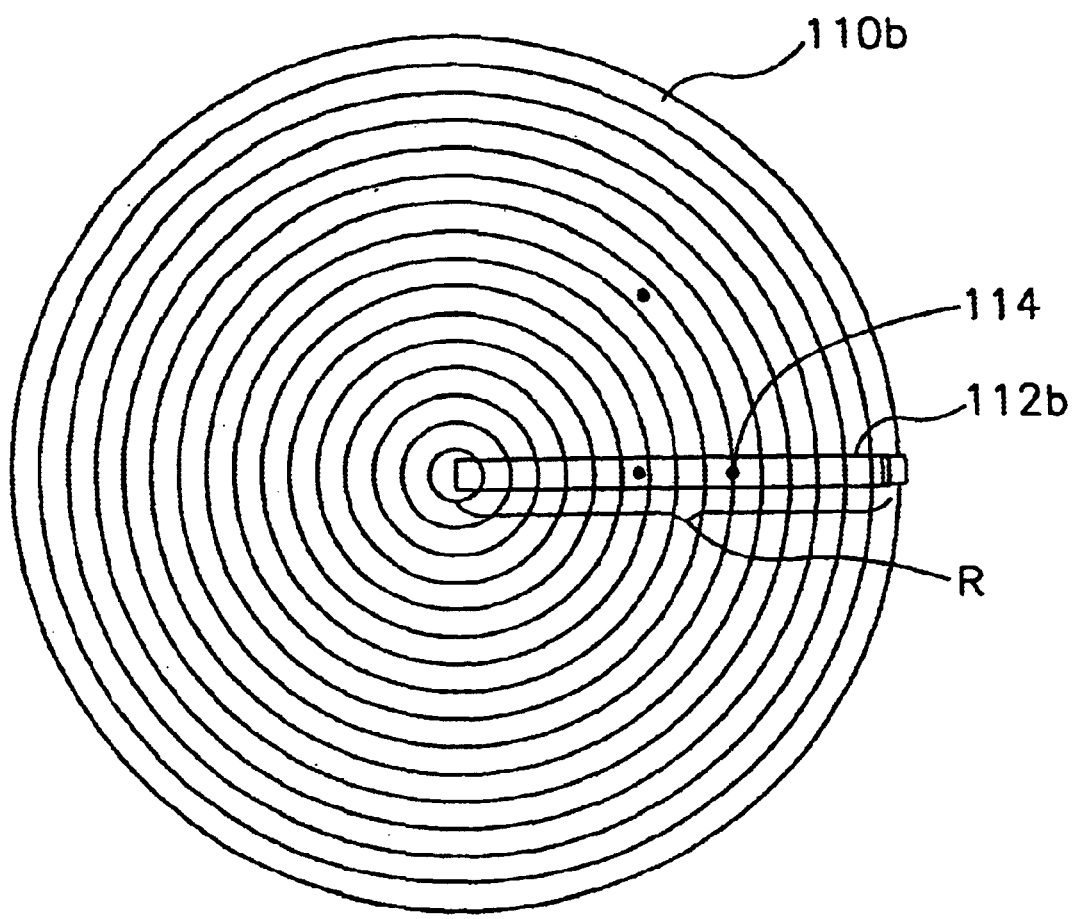

FIGS. 9A and 9B show images of the optical data which are obtained by inspecting the polishing pad according to the method of the present invention. FIG. 9A shows image data 110a obtained from a defect-free normal polishing pad, and FIG. 9B shows image data 110b obtained from a polishing pad to be inspected. The image data 110a and 110b are obtained by radiating, collecting and outputting the optical data from predetermined areas 112a and 112b of the normal polishing pad and the polishing pad to be inspected, and by outputting the optical data of the whole polishing pad, wherein the optical data is outputted depending on the predetermined angles along the R axis. In this manner, the user can recognize the defect s114 which exist in the polishing pad from the image data.

Figure 10:
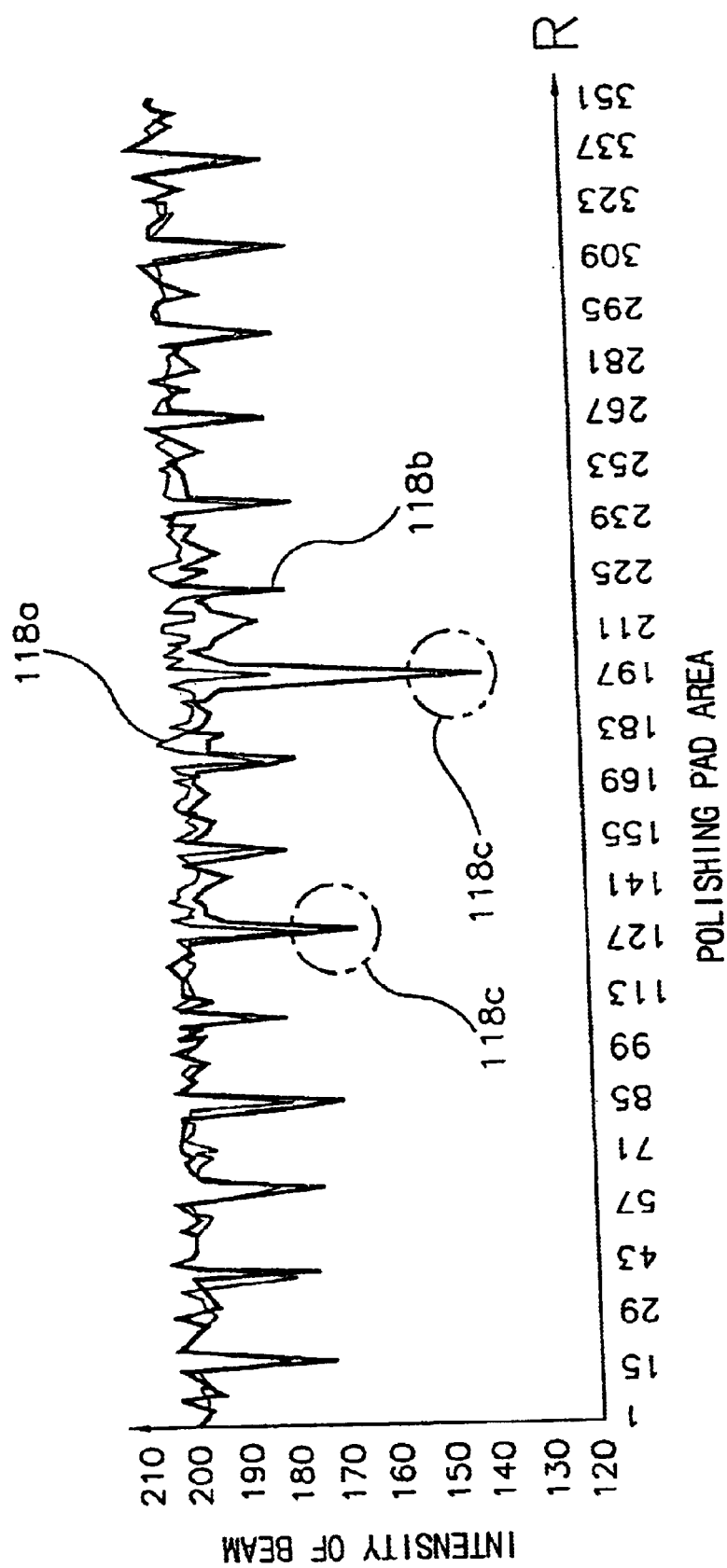
FIG. 10 is a graph showing optical data which are converted to analog signals and detected at predetermined areas of the images shown in FIGS. 9A and 9B.

FIG. 10 is a graph of the beam intensity over the polishing pad area, and shows the analog optical data signals detected from the predetermined areas 112a and 112b shown in FIGS. 9A and 9B. The optical data 118a detected from the normal polishing pad becomes the reference data. The reference data 118a is compared with the optical data detected from the polishing pad to be inspected. If the difference between the optical data 118a and 118b exceeds a predetermined value, it is determined that the defect is generated in the polishing pad.

Since grooves are regularly formed on the surface of the polishing pad (shown by the downward projecting spikes at regular intervals in FIG. 10), the intensity of the beam also regularly varies coincident with the grooves. However, as mentioned above, the irregular optical data 118c caused by defects can be discriminated from the optical data 118a which are detected from the normal polishing pad.

However, since the variation of the optical data caused by the grooves may have an influence on the signal to noise ratio, the optical data 118a detected from the normal polishing pad and the optical data 118b detected from the polishing pad to be inspected are subjected to an arithmetic smoothing process, before being compared with each other so as to detect the defect.

Figure 11:
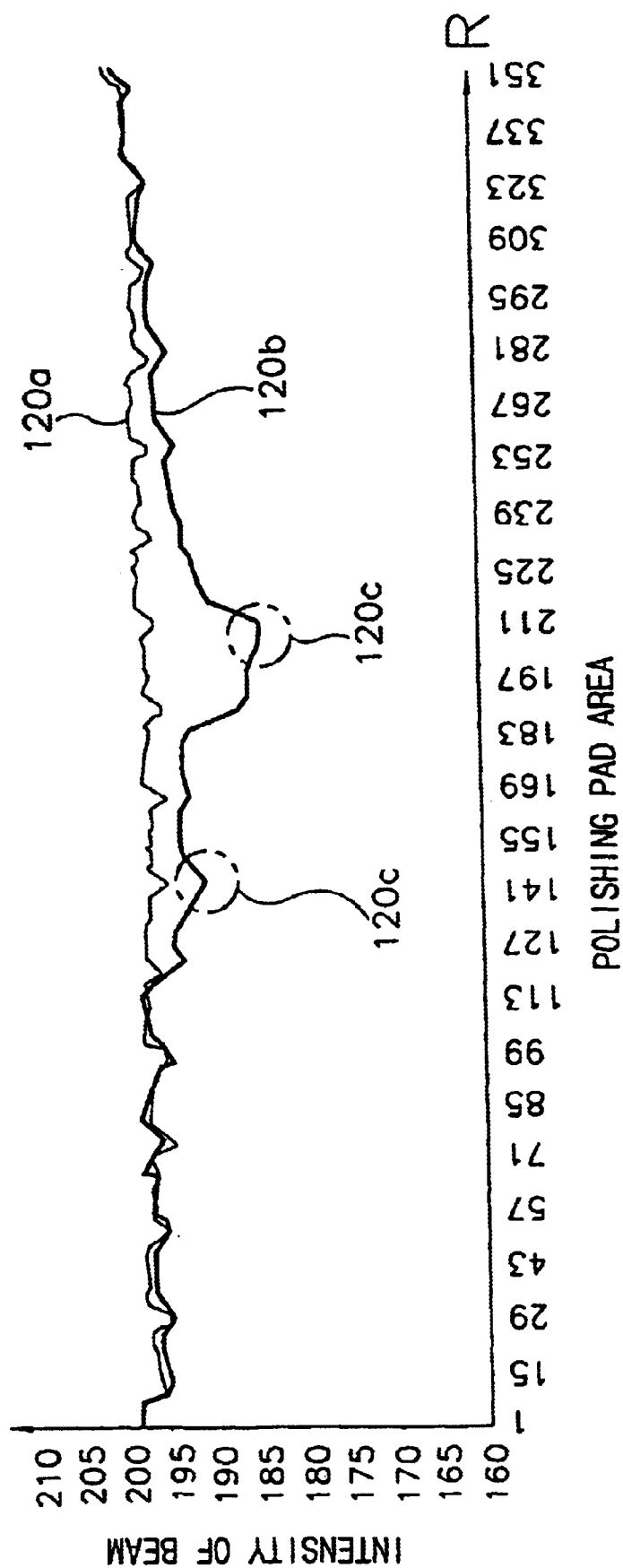
FIG. 11 is a graph showing optical data which are obtained by smoothing the optical data shown in FIG. 10.

FIG. 11 is a graph of the beam intensity over the polishing pad area, and shows optical data which are obtained by smoothing the optical data shown in FIG. 10. The optical data 118a detected from the normal polishing pad and the optical data 118b detected from the polishing pad to be inspected are subjected to a smoothing process so that smoothed optical data 120a and 120b are obtained along the R axis. For the smoothed optical data 120a and 120b, the irregularities of the optical data caused by the roughness of the surface of the polishing pad are reduced. Accordingly, the operator can easily recognize the defects 120c and their respective positions by comparing the smoothed optical data 120a and 120b with each other.

Figure 12:
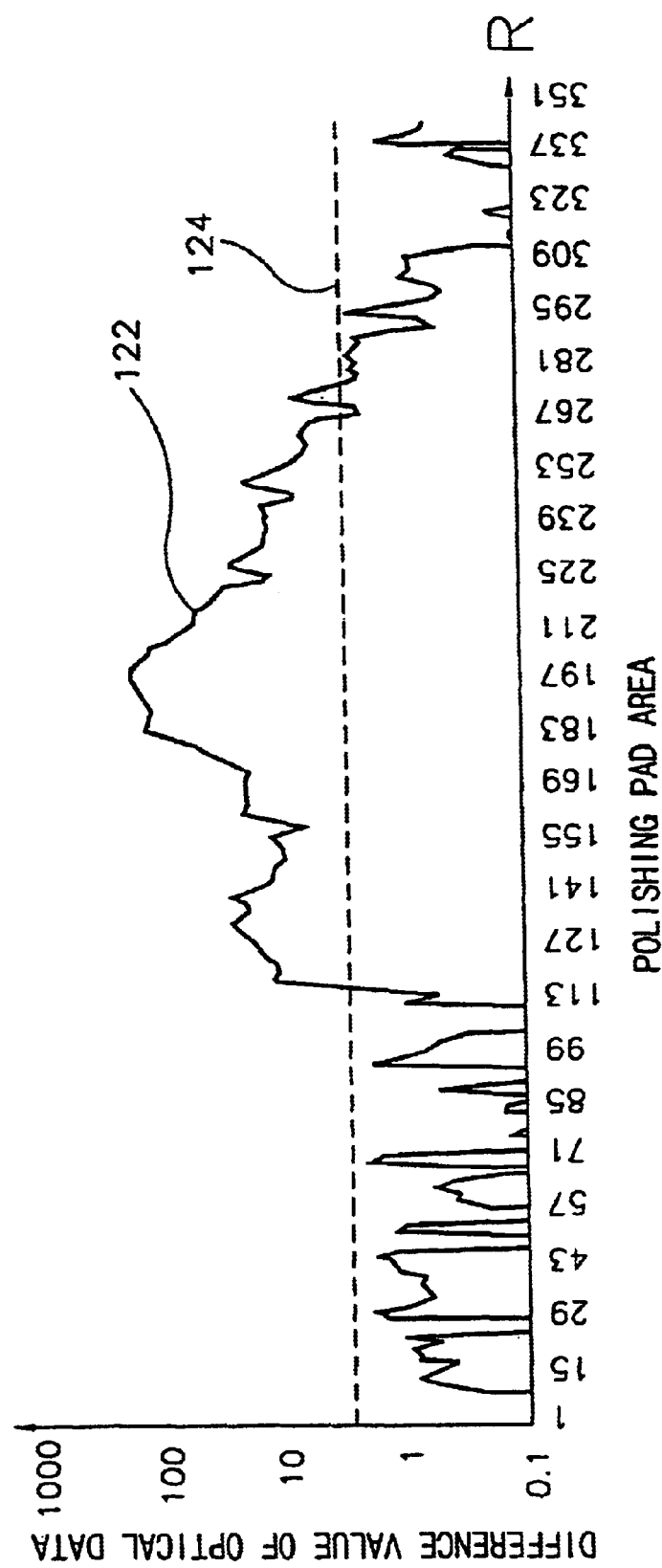
FIG. 12 is a graph for explaining a defect detecting method by comparing the data shown in FIG. 11.

FIG. 12 is a graph of difference values over the polishing pad area, for use in describing a defect detecting method by comparing the optical data shown in FIG. 11. Referring to FIG. 12, the difference values between the optical data along the R axis are obtained in order to discriminate the optical data 120a, which is obtained by smoothing the optical data 118a detected from the normal polishing pad, from the optical data 120b, which is obtained by smoothing the optical data 118b detected from the polishing pad to be inspected. Also, the difference values are squared so as to clearly discriminate the difference values. Then, the difference values representing the optical data are presented on a logarithmic scale. The defect is detected by comparing the obtained data 122 with a predetermined reference or threshold value 124. The threshold value 124 is variable, and can be determined by one of ordinary skill in the art without undo experimentation. The threshold value 124 is a function of the degree of polishing required by a particular process. Different companies may reach different conclusions as to what a satisfactory threshold level is, depending on the process, the device, the cost to produce, the selling price, and other factors.

As described above, the present invention inspects for polishing pad defects using optical data obtained from the surface of the polishing pad. Preferably, the polishing pad is inspected before the polishing pad is placed on the polishing device so that the polishing pad does not cause wafer defects during the polishing process. However, an operator can easily inspect for defects during idle times in the polishing process, or after the polishing process, to ensure rapid follow-up if a defect is detected. Accordingly, scratches on the wafers are prevented during the polishing process, thereby improving the yield rate of the semiconductor device.

Although preferred embodiments of the invention have been described, it will be understood by those skilled in the art that the present invention should not be limited to the described preferred embodiment, but various changes and modifications can be made within the spirit and scope of the invention as defined by the appended claims.

What is claimed is:

1. A method for inspecting a polishing pad, comprising:
   obtaining reference data from a surface of a reference polishing pad which is known to produce a defect-free wafer;
   radiating a beam onto a region extending across a radial unit area of the polishing pad to be inspected while rotating the polishing pad such that the radial unit area scan a surface of the rotating polishing pad;
   obtaining empirical optical data of the radial unit area scanning the surface of the polishing pad to be inspected;
   comparing the reference data with the empirical data to determine whether a defect is present in the radial unit area scanning the surface of the polishing pad; and
   determining a position of a defect in the polishing pad by using both a position of the defect in the radial unit area and a rotational angle of the polishing pad from a reference point.

2. The method as claimed in claim 1, the reference and empirical data are beam intensity data for image display of a surface of the polishing pad.

3. The method as claimed in claim 2, wherein the beam intensity data are outputted as electric signals by converting optical data into electric signals.

4. The method as claimed in clam 1, further comprising smoothing the reference data and empirical data prior to comparing the reference data and empirical data, wherein the smoothing includes,
   dividing reference data and the empirical data into a plurality of data areas;
   obtaining an average reference data value and an average empirical data value from the respective data areas; and
   comprising the average reference data value and the average empirical data value.

5. The method as claimed in claim 1, further comprising activating an alarm when the defect is detected.

6. The method as claimed in claim 1, further comprising displaying an image of the polishing pad to enable visual detection of the polishing pad defects.

7. An apparatus for inspecting a polishing pad, comprising:
   a stage for placing a polishing pad thereon, said stage including a rotating motor for rotating the stage;
   a beam source for radiating a beam onto a radial unit area of a surface of the polishing pad;
   an output part for continuously outputting an empirical optical data for image display of the radial unit area of the polishing pad;
   a defect detecting part connected to the output part for comparing reference data with the empirical data to determine whether a defect is present in the radial unit area of the polishing pad; and
   a defect position detecting part connected to the defect detecting part for determining a position of a defect in the polishing pad by using both a position of the defect in the radial unit area and a rotational angle of the polishing pad from a reference point.

8. The apparatus for inspecting a polishing pad as claimed in claim 7, wherein the output part comprises a plurality of opto-electric converting devices for converting the intensity of the reflection beam into electric signals.

9. The apparatus for inspecting a polishing pad as claimed in claim 7, wherein the output part further comprises a converter for converting analog optical data outputted from the opto-electric converting devices into digital signals.

10. The apparatus for inspecting a polishing pad as claimed in claim 9, wherein the plurality of opto-electric converting devices are spaced from a center of the polishing pad by a predetermined distance, and have predetermined angles with respect to the center of the polishing pad.

11. The apparatus for inspecting a polishing pad as claimed in claim 7, wherein the defect detecting part comprises,
   a storing part for storing the reference data outputted from the output part;
   an input part containing the empirical data outputted from the output part; and
   a defect checking part capable of comparing the reference data in the storing part and the empirical data in the input part.

12. The apparatus for inspecting a polishing pad as claimed in claim 7, further comprising a control part connected to the determine part for ceasing a polishing pad inspection process, and for generating an alarm signal when the defect is detected on the polishing pad being inspected.

13. The apparatus for inspecting a polishing pad as claimed in claim 7, further comprising a monitor connected to the defect detecting part for displaying image of the polishing pad.

14. The apparatus for inspecting a polishing pad as claimed in claim 7, wherein the position detecting part includes means for calculating (I) a rotating angle of the polishing pad with respect to a reference point, and (ii) a distance from a center of the polishing pad along a radius thereof so as to detecting the position of the defect.

15. A polishing device comprising:
a polishing head which suctions a wafer and rotates while pressing the wafer;
a platen which is rotated by a rotating shaft installed at a lower portion thereof and on which a polishing pad for polishing the wafer is attached;
a beam source for radiating a beam onto a radial unit area in a surface of the polishing pad on the platen;
an output part for continuously outputting an empirical data for image display of the radial unit area on the polishing pad;
a defect detecting part connected to the output part for comparing reference data with the empirical data to determine whether a defect is present in the radial unit area of the polishing pad; and
a defect position detecting part connected to the determine part state for determining a position of a defect in the polishing pad by using both a position of the defect in the radial unit area and a rotational angle of the polishing pad from a reference point.

16. The polishing device as claimed in claim 15, wherein the output part comprises a plurality of opto-electric converting devices for converting the intensity of the reflection beam into electric signals.

17. The polishing device as claimed in claim 16, wherein the plurality of opto-electric converting devices are spaced from a center of the polishing pad by a predetermined distance, and have predetermined angles with respect to the center of the polishing pad.

18. The polishing device as claimed in claim 15, the defect detecting part comprises,
a storing part for storing the reference data outputted from the output part;
an input part containing the empirical data outputted from the output part; and
a defect checking part capable of comparing the reference data in the storing part and the empirical data in the input part.

19. The polishing device as claimed in claim 15, wherein the position detecting part includes means for calculating (I) a rotating angle of the polishing pad with respect to a reference point, and (ii) a distance from a center of the polishing pad along a radius thereof so as to detecting the position of the defect.

* * * * *